United States Patent [19]

Hueck

[11] Patent Number: 5,033,298

[45] Date of Patent: Jul. 23, 1991

[54] PROCESS AND AN APPARATUS FOR TESTING SPRING-LOADED ELEMENTS HAVING ESSENTIALLY LINEAR PITCH OF SPRING

[75] Inventor: Manfred Hueck, Vaterstetten, Fed. Rep. of Germany

[73] Assignee: Industrieanlagen-Betriebsgesellschaft mbH, Ottobrunn, Fed. Rep. of Germany

[21] Appl. No.: 411,521

[22] PCT Filed: Mar. 11, 1988

[86] PCT No.: PCT/EP88/00193

§ 371 Date: Sep. 26, 1989

§ 102(e) Date: Sep. 26, 1989

[87] PCT Pub. No.: WO88/07669

PCT Pub. Date: Oct. 6, 1988

[30] Foreign Application Priority Data

Mar. 30, 1987 [DE] Fed. Rep. of Germany ....... 3710552
Apr. 10, 1987 [DE] Fed. Rep. of Germany ....... 3712180

[51] Int. Cl.⁵ .......................... G01L 1/04; G01N 3/26
[52] U.S. Cl. ..................................................... 73/161
[58] Field of Search .................... 73/161, 662

[56] References Cited

U.S. PATENT DOCUMENTS

| 277,898 | 5/1883 | Harty | 73/161 |
| 2,222,892 | 11/1940 | Wunderlich | 73/161 |
| 2,835,129 | 5/1958 | Reiser et al. | 73/161 |

FOREIGN PATENT DOCUMENTS

| 641299 | 11/1979 | U.S.S.R. | |
| 0953518 | 8/1982 | U.S.S.R. | 73/161 |
| 2167523 | 5/1986 | United Kingdom | |

OTHER PUBLICATIONS

Levitanus et al., "Accelerated Corrosion-Fatigue Tests of Coiled Springs", Russian Engineering Journal, vol. 11, No. 10, pp. 24–26 (undated).

Primary Examiner—William A. Cuchlinski, Jr.
Assistant Examiner—Alvin Wirthlin
Attorney, Agent, or Firm—Burgess, Ryan & Wayne

[57] ABSTRACT

A process and an apparatus for testing spring elements includes supporting at least one first spring element between first arms of a pair of lever beams, each having a stationary bearing, and at least one second spring element, between second arms of the pair of lever beams, and cyclically oscillating at least one of the lever beams at a frequency which essentially corresponds to the first resonant frequency of the oscillatory circuit formed by the lever beams and the spring elements, and the lever beams being oscillated in phase opposite to each other.

11 Claims, 6 Drawing Sheets

PROCESS AND AN APPARATUS FOR TESTING SPRING-LOADED ELEMENTS HAVING ESSENTIALLY LINEAR PITCH OF SPRING

BACKGROUND OF THE INVENTION

The invention concerns a process and an apparatus for testing resilient elements.

The expression "resilient elements" refers to elements having a resiliency over a certain spring range. These include elements that serve for spring loading such as coil springs, rubber springs, leaf springs or the like, and, at least partly, resilient elements serving an additional or different purpose such as shock-absorber legs for motor vehicles or skis for alpine, jumping or cross-country skiing.

For developing such elements for final control in the production or for vendor inspection of external parts, the elements must be dynamically tested under load conditions close to those existing in use. This means that the elements are exposed, for example, to an endurance test of usually up to about $10^6$ load cycles.

In one kind of formerly used test bench (East German Patent No. 656), there are provided eccentric drives to introduce test deformations in the clamped resilient elements. This kind of drive has, on one hand, the disadvantage that the testing frequency must be relatively low since, otherwise, the forces due to inertial masses that cannot be balanced lead to bearing loads, etc. that can no longer be neglected. The low frequency of the load reversal, in turn, leads to an extremely long testing time on the individual part which is a hindrance for the development of such elements and considerably delays sample testing of production parts. Another problem in testing benches with eccentric drives is that only oscillation tests with constant amplitudes can be performed since the adjustment of the height of the eccentric drives is extremely difficult, and can only be carried out while the apparatus is idle.

To obtain stress profiles close to in use condition in which a plurality of amplitudes are used, servo-hydraulic test equipment is known. Servo-hydraulic test equipment is not only extremely expensive to produce, but also has a high wear and power requirement, so that operation is very costly. Especially in the testing of leaf springs (such as for trucks), just the cost of operation of the equipment in a servo-hydraulic system is extremely high. As one example makes clear, for testing a 10 ton leaf spring with 300 mm stroke and $10^6$ stress cycles which are passed at a frequency of 2 Hz, the cost of operation falls in the range of about 20,000 German Marks, since the hydraulic energy applied in spring loading is converted to heat during spring unloading.

German Patent Application No. 25 22 890 has further disclosed servo-hydraulic test equipment where an auxiliary weight is attached to a coil spring to be tested so that a servo-hydraulically excited oscillation system results. Although this arrangement has a clearly lower consumption of energy, oscillations are excited on the show place, which is not only disturbing and requires an expensive bench, but also represents a loss of energy.

The principle of material testing which makes use of the test sample in an oscillation system is also known from German Patent Application No. 25 33 373 or U.S. Pat. No. 4,539,845. However, with both known systems, only oscillations with very low amplitudes can be excited, thus requiring the use of springs having a large displacement.

East German Patent No. 216,317 discloses a process wherein a mass element is introduced between two coil springs placed in a row and fastened by the ends, so that a series oscillatory circuit results. The mass element is reciprocally moved directly over a linear drive at the resonant frequency of the system. In this arrangement, the whole system is dislocated in oscillations and thus, the above described disadvantages result.

Thus, the problem, as a whole, is that all known processes or systems entail high costs of operation and are limited in their working speed (resonant frequency) as a result of the losses caused by the system.

The periodical "Soviet Inventions Illustrated", Week B40, Nov. 14, 1979, No. J5481 B/40, London, G.B., discloses a process and an apparatus for testing resilient spring elements which are supported between two lever beams and are in opposed phase so as to be offset in their oscillations. This phase opposition of the levers is obtained by gear connections between the levers. Due to this connection between the levers, the arrangement is, on one hand, inflexible regarding the adjustment for receiving different test samples and, on the other hand, with the gear connection, oscillations are produced that adversely affect the results of the test. Finally, a very high torque has to be applied when starting up the installation.

FR-A 2,292,966 discloses a system wherein two springs are clamped between both ends of a lever and a bench. The arrangement is to be operated by resonant frequency. As described above, such an arrangement is objectionable insofar as forces of inertial masses considerably limit the testing frequency and also the testing amplitudes.

Based on the above prior art, the problem solved by this invention is to develop a process and an apparatus of the above mentioned kind in the sense that resilient elements can be tested quicker than formerly accomplished and in a simple, inexpensive way.

OBJECTS AND SUMMARY OF THE INVENTION

This problem is solved with regard to the process by the fact that at least one first resilient element is supported between first arms of a pair of lever beams, each having a stationary bearing, and at least one second resilient element is supported between second arms of the pair of lever beams, and the frequency at which at least one of the lever beams is oscillated by means of an oscillation exciter, substantially corresponds to the first resonant frequency of the oscillatory circuit formed by the lever beams and the resilient elements, and the lever beams are oscillated in an opposed phase that is, 180° out of phase.

Therefore, the essential point of the invention is that there is built up a resonant-capable system wherein at least two resilient elements are in operative connection with each other in a manner such that when one resilient element is unloaded, the other is loaded, and vice versa, the test or stress frequency corresponding to the resonant frequency of the system which is determined by the spring tensions and the moments of inertia of the system.

If leaf springs are tested, it is preferred to test, instead of one leaf spring on each side of the lever beams, two leaf springs connected in series and communicating by their outer ends via intermediate pieces. In this manner, on one hand, four leaf springs are simultaneously tested and, on the other hand, the end points of the leaf springs remain at rest during the test. It is, of course, always possible to clamp in parallel a plurality of test samples as "resilient elements". With a higher rigidity of the spring, the resonant frequency of the system is raised so that the testing frequency increases and thus, the duration of the test diminishes. A limitation of the testing frequency according to the above results, is on one hand, by the power of the oscillation needed as a result of the damping in the system and, on the other hand, by the heating of the test samples. Thus, for example, in laminated leaf springs having their own high damping (especially after several stress cycles), a relatively low testing frequency must be selected, as otherwise, the springs become too hot and the results of the test do not correspond to the actual use conditions.

With the process and apparatus according to the invention, it is easily possible to use during the testing, variable amplitudes without the high costs of energy resulting in servo-hydraulic systems.

When testing skis, it is possible, by adequate support asymmetric in respect to the longitudinal axis of the ski, to produce a torsion simultaneously with the bending.

For testing coil springs, it is desirable in certain problems to test individual spring coils since the individual variables can then be separately tested and evaluated. Examples of such variables are influences of the material, shot-peening parameters, surface protection, corrosion problems in dynamic use, mean stress influences, static parameters of creep strength, like setting evaluation of endurance limit. By the process and system according to the invention, the central part of the individual spring coil remains stationary during the whole stress cycle. Therefore, it is possible to apply, in the central part, transducers (such as strain gauges), whose leads are not exposed to loading of any kind. It is further possible to submerge the middle portion in corrosive substances (salt water) during the test, which is not possible, at least at high loading frequencies, when vibrating complete springs. In addition, the processing of cracking can be well observed.

Electric or hydraulic drives are suitable as oscillation exciters depending on the performance needed. These are preferably arranged, both removably and replaceably, as are the lever beams, so that the whole apparatus can be adapted to the kind of sample to be tested.

Other essential features of the invention can be seen from the description that follows of preferred embodiments of the invention which are described in detail with reference to the figures.

DETAILED DESCRIPTION OF THE PREFERRED EMBODIMENTS

Figure 1:
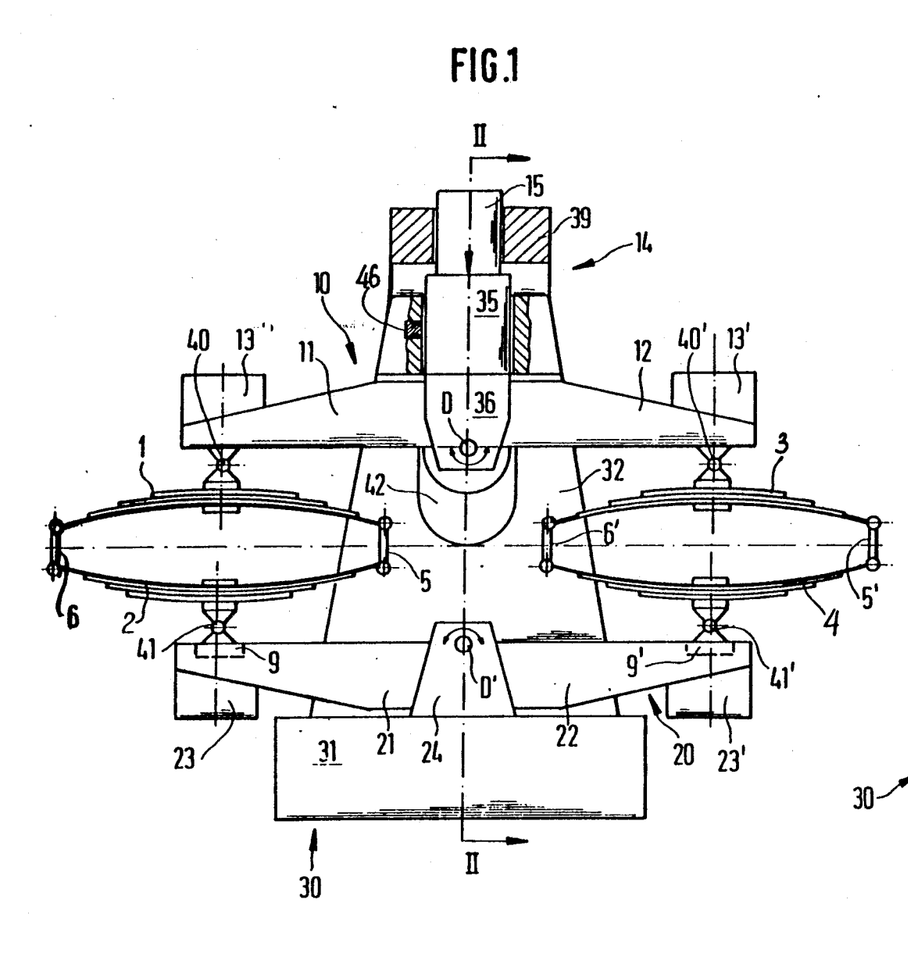
FIG. 1 is a diagrammatic partial sectional front view of a test bench according to one embodiment of the invention for use with flat springs.
Figure 2:
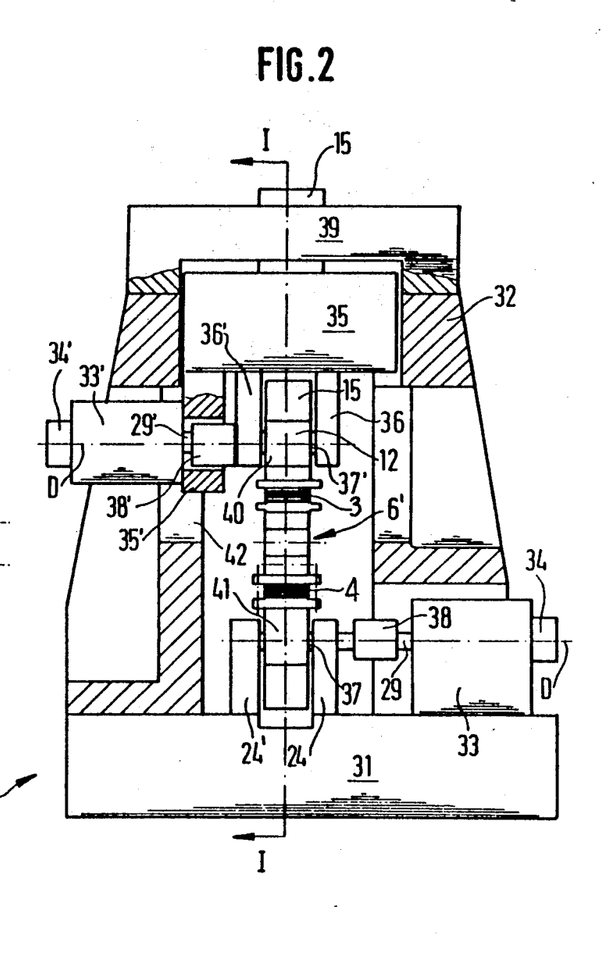
FIG. 2 is a sectional view of the test bench of FIG. 1, taken along line II—II thereof.

The following is a description, in detail, of a first preferred embodiment of the invention according to FIGS. 1 and 2, wherein flat springs are shown in the arrangement as test samples.

The figures disclose a machine frame 30 which comprises a base 31 and a post 32, two lever beams 10, 20 are supported, one above the other, on bearings in a manner such that they can reciprocally tilt about rotation axes D and D'. As shown in FIG. 2, the lower bearing comprises supports 24, 24' fastened on the machine frame 31, while the upper bearing comprises supports 36, 36' fastened on a guide 35 and are movable in a direction toward and away from the lower bearing supports 24, 24' via prestress means 15 such as a hydraulic device which is fastened on a crosshead 39 on the post 32. Thus, the guide 35, together with the prestress means 15 constitutes a prestressing device 14 (See FIG. 6) with which the test samples can be prestressed in a manner such that the stress cycle can be both a tension load and (as shown in FIGS. 1 and 2) a pressure load exclusively in the area of interest.

The rotation axes D and D' divide each lever beam 10, 20 into a left arm 11 or 21 and a right arm 12 or 22. At the end of the arms 11, 12, 21, 22, there are provided clamping devices 40, 40', 41, 41' respectively, between which the test samples can be clamped. Further, added weights 13, 13', 23, 23' respectively, can be mounted at the ends of the arms, the mounting being preferably such that the added weights are movable in a direction toward the axes of rotation D, D' of the respective lever beams 10, 20, so that the moments of inertia of the lever beams 10, 20 are adjustable by the position of the added weights in respect to o the axes of rotation D or D', whereby it is possible, in turn, to adjust the testing frequency.

Clamping devices 41, 41' are provided with dynamometers 9, 9' for measuring the forces introduced in the test samples 1 to 4.

In the embodiment of the invention shown in FIGS. 1 and 2, in order to test leaf springs, two leaf 1 and 2 are interconnected at their ends by intermediate pieces 5 and 6 to form a spring series and two leaf springs 3 and 4 are interconnected at their ends by intermediate pieces 5' and 6' to form a spring series, while the respective central points of suspension of the leaf springs 1 to 4 are fixed on the clamping devices 40, 41, 40' and 41'. In this manner, on one hand, the ends of the leaf springs are at rest during oscillation thereof, depending on the actual conditions of operation and, on the other hand, all four leaf springs can be simultaneously tested.

The oscillation exciters can be drive motors 33, 33' whose output shafts 29, 29' are fixedly connected via shaft couplings 38, 38' with bearing axles 37, 37' of the lever beams 10, 20, so that rotation of the motor shafts 29, 29' leads to tilting or rocking movements of the lever beams 10, 20. In the embodiment of the invention shown in FIGS. 1 and 2, the lower motor 33 is secured to the machine frame while the upper motor 33' is bolted on a portion 35' of the guide 35 and projects through an opening 42 in the post 32 of the machine frame 30. Each motor 33, 33' is provided with an angle transducer 34, 34', the output signals of which are used for controlling frequency, amplitude and mean or zero position of the movements, as described in detail hereinbelow.

Depending on the power requirement or on the frequency of movement to be adjusted, the motors 33, 33' can be respectively hydraulic motors, hydraulic swivel motors, or adequately designed electromotors. The lever beams 10, 20 and the motors 33, 33' are preferably replaceable so as to be adaptable in regard to the spring elements to be tested. When testing, for example, non-laminated leaf springs (as shown in FIGS. 1 and 2), which have an extremely low damping, weaker motors will serve the purpose. Further, it is possible in the case of such springs, due to lower damping to test at higher frequencies since the springs become less heated so that lighter lever beams or those with lower moments of inertia can be used. Due to the fact that the distance between lever beams 10, 20 is adjustable, it is possible, at the beginning of the test, to mount the spring elements to be tested first when the guide 35 is raised and afterwards when the guide 35 is lowered, and the guide is fixed by a clamping element 46, to perform the test under conditions close to realistic conditions.

Figure 3:
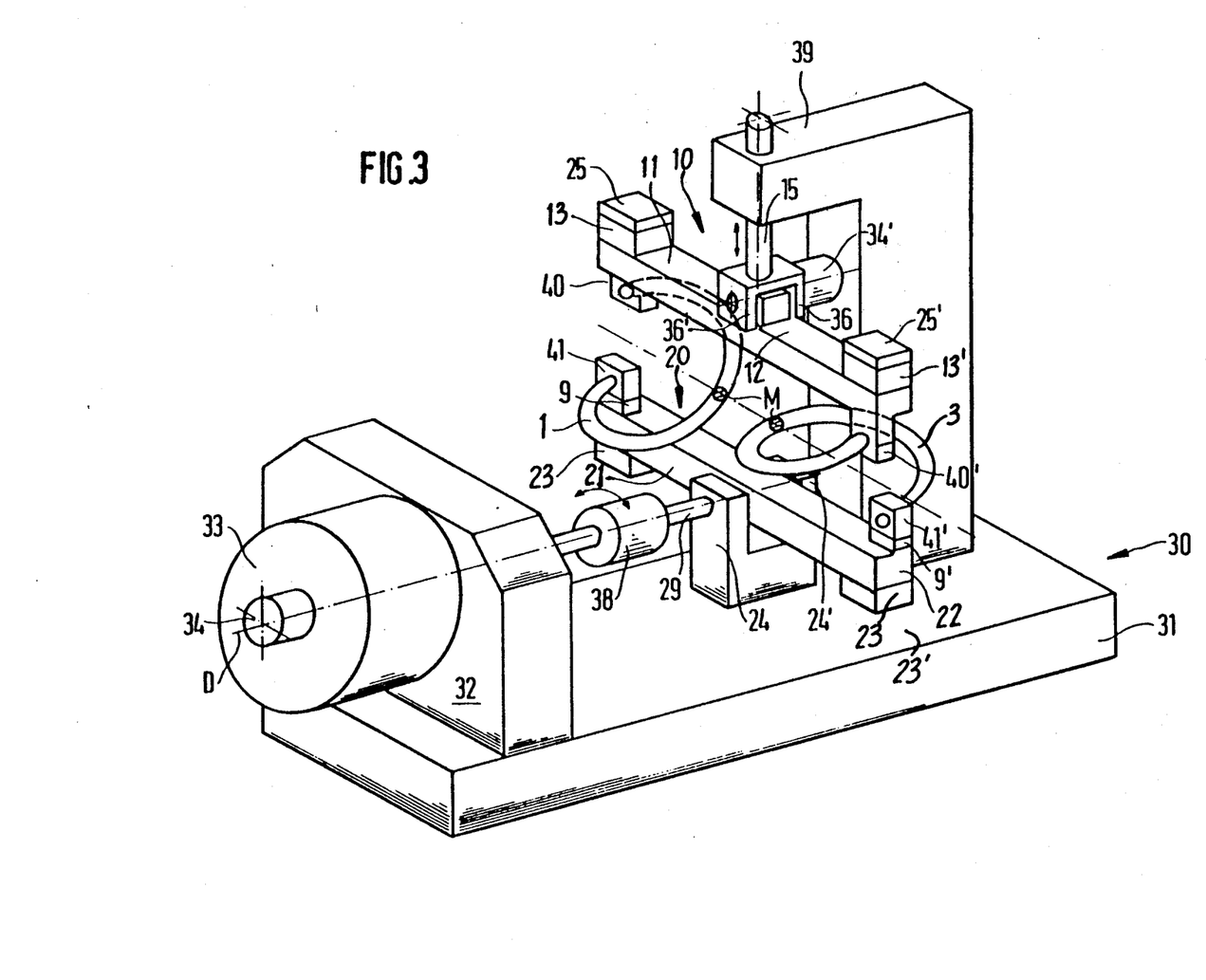
FIG. 3 is a diagrammatic perspective view of a test bench according to another embodiment of the invention, for use with separate coils of coil springs.

The embodiment of the invention shown in FIG. 3, wherein the same or equally operating parts are designated with the same numbers, is suitable for testing spring elements of small dimensions.

In this preferred embodiment of the invention, there is secured to a post 32 of the machine frame 30 only one drive motor 33 which drives the lower beam 20. The upper lever beam 10 has no drive motor, but only an angle transducer 34'.

While in the embodiment of the invention shown in FIGS. 1 and 2, the moments of inertia of the motors and the drive shafts thereof are not important compared to the moments of inertia of the lever beams, in the embodiment of the invention shown in FIG. 3, the moment of inertia of the drive (motor, coupling, shafts) can not be neglected. For this reason, there are provided, in addition to the added weights 13, 13', 23, 23' on both lever beams 10, 20, weights 25, 25' on lever beam 10, 20, so that the moments of inertia of both lever beams 10 and 20, together with all weights moved therewith, are identical.

When testing individual spring coils, as shown in FIG. 3, points on the spring coils which lie on a plane midway between both lever beams 10 and 20 (shown in dotted lines in FIG. 3) remain stationary. Consequently, points M for measuring are available to applicate, strain gauges or the like, it being also possible to use very sensitive mechanical transducers or transducers having sensitive lead-ins, since the points M do not oscillate during the test.

It is especially advantageous here, at the start of a test to search for the resonant frequency of the system, so that very high frequencies at low amplitudes can be used at the start of the operation so as to prevent an equal-phase oscillation of the two lever beams 10 and 20, which would entail a movement of the points M.

Figure 4:
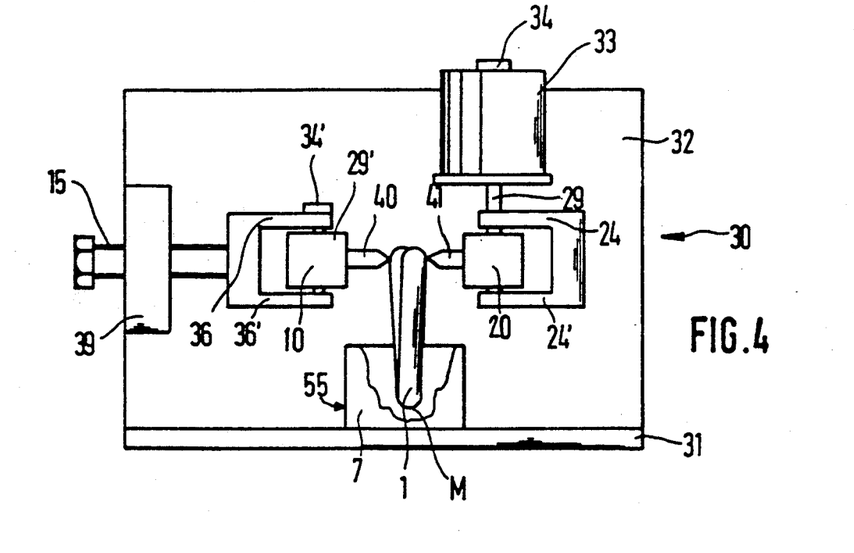
FIG. 4 is a diagrammatic front view of another preferred embodiment of the test bench of FIG. 3.
Figure 5:
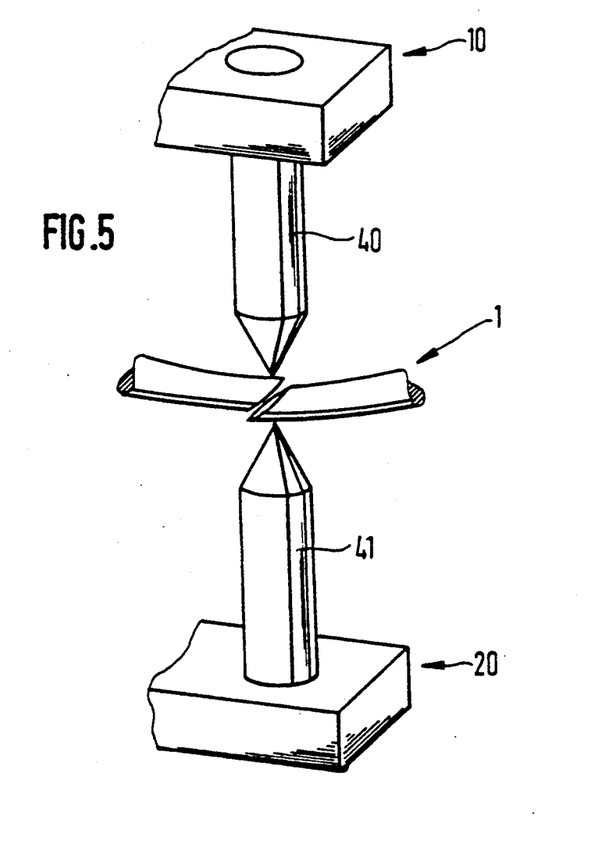
FIG. 5 is a sectional view of the spring bearing support of the apparatus according to FIG. 4.
Figure 6:
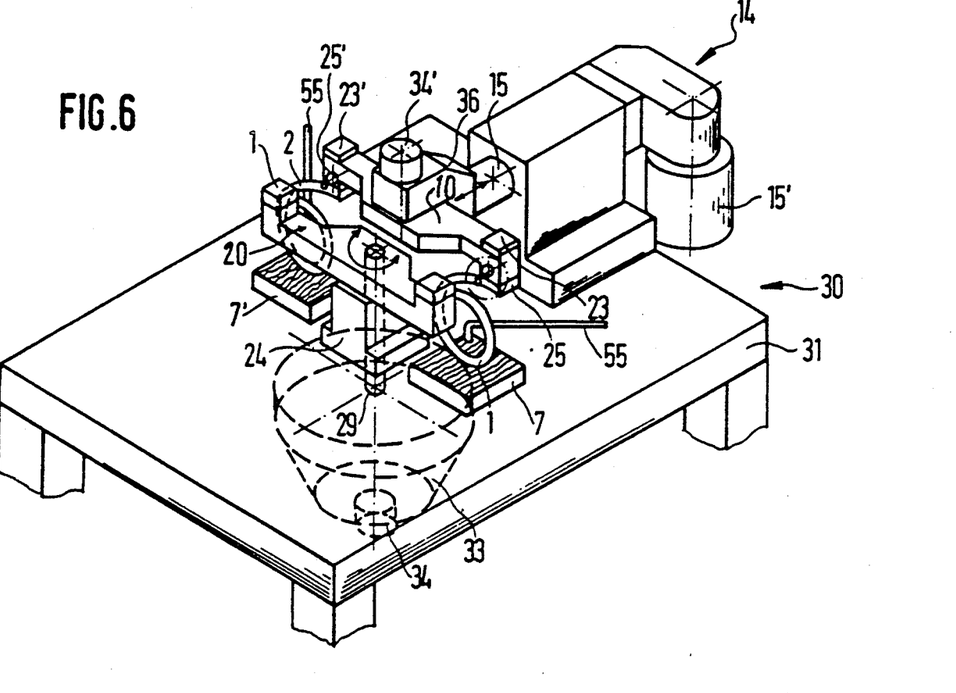
FIG. 6 is a perspective view of another embodiment of a test bench, similar to that of FIG. 3.

Of special advantage for testing separate spring coils are the embodiments of the invention shown in FIGS. 4 to 6, wherein the variants shown in FIGS. 4 and 6 differ from the embodiment shown in FIG. 3, in the first place, by the fact that the lever beams 10, 20 oscillate in a horizontal plane. By virtue of this arrangement, it is possible to allow separate spring coils to hang down and to situate the outlet openings of spraying pipes 55 above the spring coils and to place 7 and 7' beneath the spring coils. Thereby, it is possible to perform corrosion tests wherein the corroding liquid can coat the stationary point of each coil spring and optionally, a transducer can be secured there at the same time.

Figure 7:
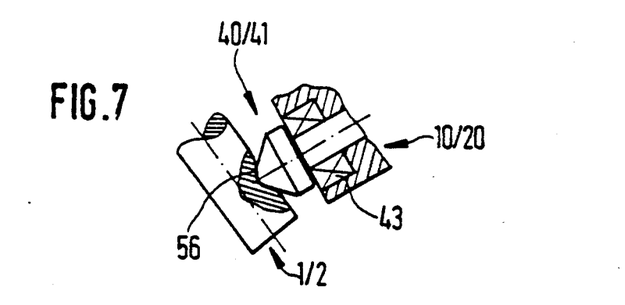
FIG. 7 is an enlarged partial sectional view of a portion of the test bench of FIG. 6.

As a result of low spring forces, spring coils can be easily and advantageously tested when mounted at the ends of clamping devices 40, and 41 (FIG. 5) which lodge in corresponding counter sunk holes at the end of the spring coil to be tested. The ends of the clamping devices are preferably placed, as shown in FIG. 7, over a roller bearing 43 arranged on the lever beam 10 or 20 so that they are free about a rotational axis. In order to prevent the introduction of further disturbing forces, the angle of the ends is smaller than the angle of the hole 56 in the test sample, as indicated in FIG. 7.

In another embodiment of the invention not shown in the figures, there is provided, instead of lever beams 10, 20, an adequate arrangement of hydraulic cylinders. Specifically, there are provided a total of four hydraulic cylinders which are coaxially disposed in pairs, both pairs preferably being situated parallel to each other. Each one of the pairs grips one spring element between the piston rods of the cylinders. The phase-opposed movement is obtained by connecting, via a duct, one cylinder of one pair with the corresponding cylinder of the other pair, a pump being provided as an oscillation exciter in at least one of the ducts.

Figure 8:
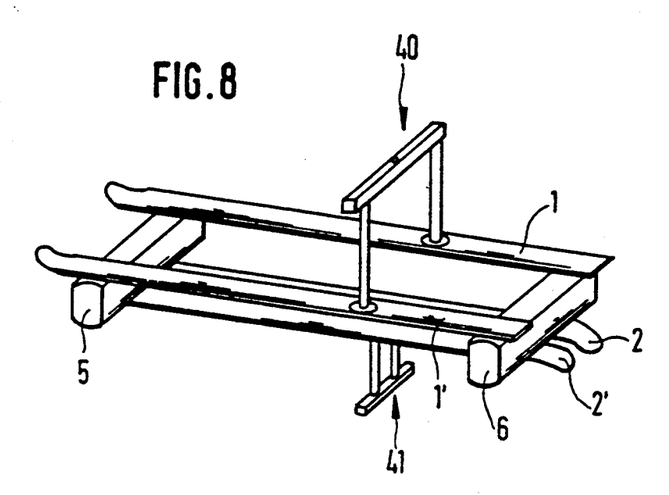
FIG. 8 is a perspective view of clamping devices for testing skis.

If skis are to be tested, clamping devices 40 and 41 are arranged as shown in FIG. 8, which resembles the basic arrangement of FIG. 1. It is of the essence here that a bending of the skis 1, 1', 2, 2' be greater than in the arrangement of FIGS. 1 and 2. This is made possible by keeping the upper pair of skis 1, 1' at a greater distance from each other between the upper clamping device 40 and the intermediate pieces 5, 6 than the lower skis 2, 2' situated between the lower clamping device 41 and intermediate pieces 5 and 6, so that both arrangements can "penetrate" with the maximum bending.

Figure 9:
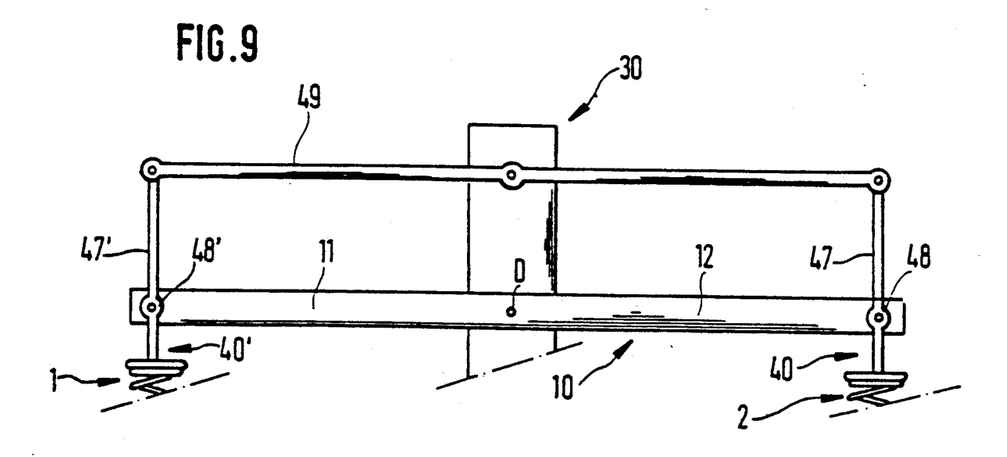
FIG. 9 is a partial front view of a preferred embodiment of clamping devices with a cross-head guide.

When spring elements that must be precisely guided in parallel are to be tested, then it is not sufficient under certain circumstances to provide clamping elements pivotally supported on the rocking beams, as shown in FIG. 1. In such case, clamping devices, as shown in FIG. 9, are advantageous. In this preferred embodiment of the invention, the clamping devices 40, 40' comprise rods 47, 47' which are pivotally supported at the ends of both arms 11 and 12 by bearings 48, 48'. At the ends opposite the springs 1, 2 to be tested, rods 47, 47' are pivotally connected with a guide bar 49 which, in turn, is axially supported on the machine frame 30. The arrangement is such that the rods 47, 47' are parallel with each other and the connecting line between the axis of rotation D of lever beam 10 and the bearing point of guide bar 49 on machine frame 30 is likewise parallel with rods 47, 47'. This parallelogram guide ensures that clamping devices 40, 40' move respectively in a straight line toward clamping devices 41, 41' (not shown) situated therebelow. In this regard, it is noted that clamping devices 41, 41' are of the same general construction as clamping devices 40, 40'. Devices of this kind are especially useful for testing coil springs with the ends thereof displaced in parallel.

Hereinbelow is described, in detail, the basic principle of the drive of the apparatus with reference to FIGS. 10 to 12, the individual elements of the arrangement being already known.

Figure 10:
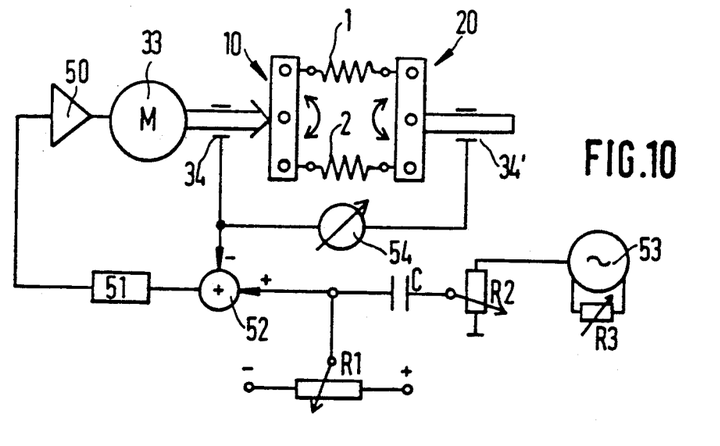
FIGS. 10-12 are diagrammatic block illustrations of adjustment circuits for oscillation exciters.

In the preferred embodiment of the invention shown in FIG. 10, there is provided only one drive motor 33, which is supplied with current via a servoamplifier 50 having its control input connected to the output of a controller 51. The controller 51 has its input connected to the output of a comparator 52 having a positive input supplied with a set point signal which is compared with the output signal of the angle transducer 34 via the inverting input of the controller. According to the value at the set point input (+), the output shaft of motor 33 rotates by a predetermined angular amplitude.

THe input set point of comparator 52 is connected via a capacitor C and an amplitude-controlling potentiometer R2 to the output of a sine wave generator 53 whose output frequency is adjustable by an adjusting member R3. In addition, a direct current potential adjustable via an adjusting means R1 is passed to the set-point input (+) of the comparator 52.

A measuring means 54 is connected between the outputs of both angle transducers 34 and 34' (for example, from the arrangement of FIG. 3), the arrangement being such that the phase between the output signals of both angle transducers 34 and 34' can be measured and displayed.

When testing a pair of spring elements, the procedure (after the above described mechanical preparations) is that the mean or zero position in which the lever beams 10, 20 are substantially perpendicular to the connecting line between their axes of rotation D and D' is first adjusted by adjusting means R1. Thereafter, by the adjusting means R3, the output frequency of the sine wave generator 53 (at low amplitude) is adjusted to a frequency that is somewhat higher than the expected resonant frequency of the system. Then, the frequency of the sine wave generator 53 is lowered until both lever beams 10 and 20 oscillate in-opposed phase, that is, 180° out of phase, which can be observed by the measuring means 54. Thereafter, the device can be adjusted to the desired amplitude, said adjustment being possible, not only manually (by the adjusting means R2), but also "program controlled" by a standardized program by which different load amplitudes are be successively applied.

Figure 11:
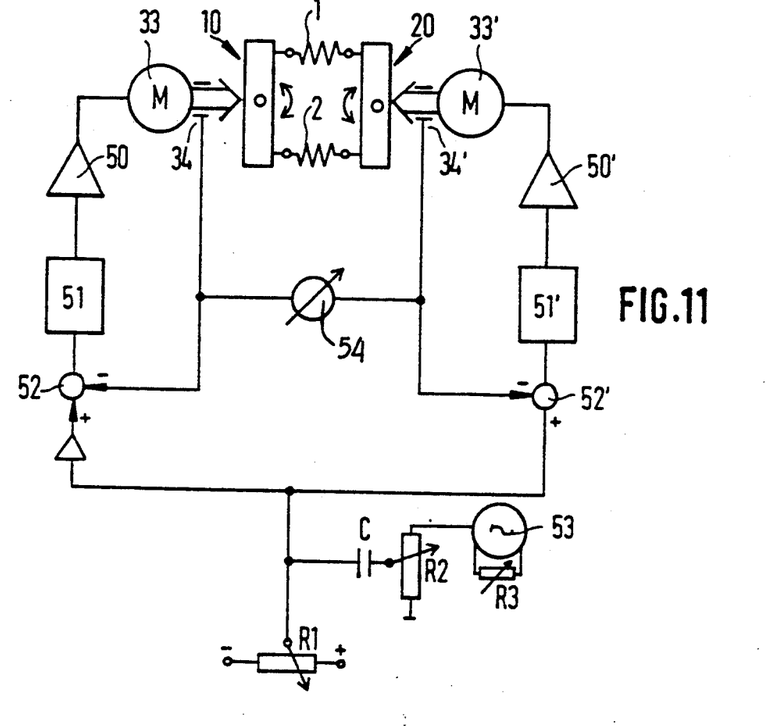

When two motors 33 and 33' are provided, as shown in FIGS. 1 and 2, then the arrangement shown in FIG. 11, which essentially comprises a duplication of the control loop shown in FIG.

10 is used, in which both drives are controlled in parallel. The reference numerals of the duplicate structures are marked with an apostrophe. For example those structures indicated by numerals 50-52 are substantially identical in function to structures identified by numerals 50'-52'.

Figure 12:
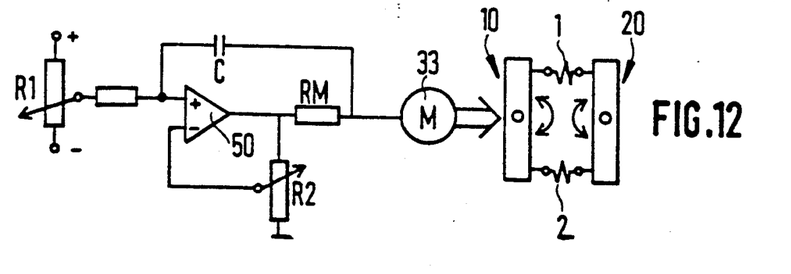

In the preferred embodiment of the invention shown in FIG. 12, for adjusting the resonant frequency, no angle transducer is provided, but rather, a precision resistor RM is provided in the connecting line between the servoamplifier 50 and the motor 33 through which a voltage proportional to the output current can be fed back via a capacitor C. The system so formed corresponds in principle to an LC oscillator where inductance and capacitance are replaced by masses and springs. Such connections are known in principle (see, for example, U. Tietze, C. Schenk, "Halbleiter-Schaltungstechnick", Springer Editing House, 1986, page 441).

There is preferably provided, not shown in the figures, an "emergency electrical power disconnect" for switching off the motor or motors which can operate in a manner such that the power requirement of the motor and the resonant frequency of the system are monitored. In case of formation of a crack in one of the springs, the damping and required power increases, the spring rigidity and the resonant frequency drops. A lowering of the resonant frequency or an increase in the power requirement by a certain fraction of the value existing at the beginning of the test can be used as the criterion for disconnecting the electrical power to stop the operation.

Another advantage of the testing apparatus explained with reference to the figures is that when dynamometers are provided, the same devices can be used both for dynamic and for static testing of spring elements.

I claim:

1. An apparatus for testing resilient elements comprising:
    two lever beams each freely pivotally supported with respect to each other on a machine frame, each lever beam being divided into a first arm and a second arm, the lever beams lying in a plane and being pivotable therein;
    each lever beam having a clamping device distally on each end of each arm, for attaching an end section of at least two resilient elements so as to couple the lever beams in said plane solely through the at least two resilient elements,
    an oscillation exciter associated with each lever beam for cyclic stressing of said at least two resilient elements, each said oscillation exciter coupled with each of said lever beams to oscillate the same; and
    means for controlling each oscillation exciter to oscillate at a frequency essentially corresponding to a first resonant frequency of an oscillation circuit formed by the lever beams and the resilient elements so that the lever beams oscillate in opposed phase relation.

2. An apparatus according to claim 1, further comprising bearing means for freely pivotally supporting said lever beams with respect to each other on the machine frame, said bearing means comprising at least one bearing and prestressing means for moving at least one beam in a plane extending through the lever beams in a direction toward and away from another bearing in a manner such that the resilient elements clamped between the lever beams can be prestressed.

3. An apparatus according to claim 1, wherein the arms are of equal length and have essentially equal inertial moments about pivoting axes of the lever beams.

4. An apparatus according to claim 2, further comprising weights movably placed on the lever beams relative to the respective bearings to adjust the inertial moments of the lever beams.

5. An apparatus according to claim 1, wherein at least one sensor is attached to at least one of the lever beams to provide an output signal related to the instantaneous position of the lever beams, the output signal being fed to the oscillation exciter as a control signal through a closed loop control circuit.

6. An apparatus according to claim 1, wherein the resilient elements each have two first coupling points spaced apart from each other which move in the same direction and a second coupling point between the two first coupling points which move in a direction opposite to the two first coupling points, wherein two pairs of intermediate pieces connect at least two of said spring-loaded elements at the first coupling points such that at least two resilient elements, connected in series, can be clamped between the clamping devices and can be simultaneously tested.

7. An apparatus according to claim 2, wherein the clamping devices comprise rods pivotally supported on the arms by hinges, the rods each having a first end adjacent the resilient elements to be coupled, said rods having a second end opposite said first end and being connected by a guide bar pivotally supported on said machine frame to form a parallelogram guide defined by the guide bar, the lever beams associated with each guide bar, and the rods.

8. An apparatus according to claim 1, wherein the clamping devices conical bearings arranged to engage depressions in opposite ends of a single coil of a resilient element to clamp the resilient element between the conical bearings.

9. An apparatus according to claim 8, wherein the lever beams are pivotally supported in a horizontal plane, and means are provided on the machine frame to spray the central portion of a spring coil to be tested with a corrosive material.

10. An apparatus according to claim 1, wherein at least one of said oscillation exciters comprise an electro-motor or hydraulic motor adjustable by a controller to a constant desired oscillatory amplitude and zero position.

11. A process for testing resilient elements, comprising the steps of:
providing a pair of lever beams, each lever beam being divided into a first and second arm, the lever beams lying in a plane and being pivotal therein, each lever beam having a stationary bearing for pivotal movement of said lever beams;
supporting at least one first resilient element between said first arms;
supporting at least one second resilient element between said second arms; wherein a first lever beam of said pair of lever beams is coupled to a second lever beam of said pair of lever beams in the same plane only by said resilient elements, and wherein said lever beams are cylically oscillated by means of an oscillation exciter associated with each lever beam at an oscillation frequency corresponding to a resonant frequency of an oscillatory circuit formed by the lever beams and the resilient elements for applying a stress cycle to the resilient elements, and wherein said frequency is adjusted such that said lever beams are oscillating in opposed phases with a phase-lock of 180°.

* * * * *